United States Patent [19]

Ramanujam et al.

[11] Patent Number: 5,421,339
[45] Date of Patent: Jun. 6, 1995

[54] DIAGNOSIS OF DYSPLASIA USING LASER INDUCED FLUOROESCENCE

[75] Inventors: Nirmala Ramanujam; Anita Mahadevan; Rebecca R. Richards-Kortum, all of Austin; Michele F. Mitchell; Sharon Thomsen, both of Houston, all of Tex.

[73] Assignee: Board of Regents, The University of Texas System, Austin, Tex.

[21] Appl. No.: 60,432

[22] Filed: May 12, 1993

[51] Int. Cl.⁶ ............................................. A61B 6/00
[52] U.S. Cl. .................................................. 128/665
[58] Field of Search .......................... 128/664–665, 128/633, 634; 607/88–93; 606/3, 14–16

[56] References Cited

U.S. PATENT DOCUMENTS

| | | |
|---|---|---|
| 4,786,813 | 11/1988 | Svanberg et al. |
| 4,930,516 | 6/1990 | Alfano et al. |
| 5,042,494 | 8/1991 | Alfano |
| 5,046,501 | 9/1991 | Crilly ............................ 128/665 |
| 5,115,137 | 5/1992 | Andersson-Engels et al. |
| 5,125,404 | 6/1992 | Kittrell |
| 5,131,398 | 7/1992 | Alfano et al. ................... 128/665 |
| 5,168,162 | 12/1992 | Dong et al. ...................... 250/339 |
| 5,174,297 | 12/1992 | Dalkuzono |
| 5,201,318 | 4/1993 | Rava et al. |
| 5,261,410 | 11/1993 | Alfano et al. |
| 5,303,026 | 4/1994 | Strobl et al. |
| 5,318,024 | 6/1994 | Kittrell et al. |

OTHER PUBLICATIONS

K. Schomaker et al., "Ultraviolet Laser-Induced Fluorescence of Colonie Tissue: Basic Biology and Diagnostic Potential", *Lasers in Surgery and Medicine*, vol. 12, pp. 63–78 (1992).

R. Cothren et al., "Gastrointestinal Tissue Diagnosis by Laser-Induced Fluorescence Spectroscopy at Endoscopy," *Gastrointestinal Endoscopy*, vol. 36, pp. 105–111 (1990).

S. Anderson-Engels et al., "Fluorescence Imaging and Points Measurements of Tissue: Applications to the Demarcation of Malignant Tumors and Atherosclerotic Lesions from Normal Tissue," *Photochemistry and Photobiology*, vol. 53, pp. 807–814 (1991).

R. Rava et al., "Early Detection of Dysplasia in Colon and Bladder Tissue Using Laser-Induced Fluorescence," *SPIE*, vol. 1426, *Optical Methods for Tumor Treatment and Early Diagnosis: Mechanisms and Techniques*, pp. 68–78 (1991).

R. Cothren et al., "Argon Ion Laser-Induced Tissue Fluoresence": Clinical Spectroscopic Studies,' *SPIE* vol. 906, *Optical Fibers in Medicine III*, Abstract only (1988).

(List continued on next page.)

*Primary Examiner*—Ruth S. Smith
*Attorney, Agent, or Firm*—Arnold, White & Durkee

[57] ABSTRACT

Apparatus and in vivo methods to distinguish normal and abnormal cervical tissue and to detect cervical intraepithelial neoplasia (CIN) in a diagnostic cervical tissue sample. Induced fluorescence intensity spectra from known normal cervical tissue and a diagnostic tissue sample are obtained from the same patient. Peak fluorescence intensity values for normal tissue samples are averaged, as are slope measurements from predetermined portions of spectra induced in both known normal cervical tissue and the diagnostic tissue sample. Peak fluorescence intensities of diagnostic tissue spectra are divided by average peak fluorescence intensity values for normal tissue in the same patient to yield relative peak fluorescence intensity values. Normal and abnormal cervical tissues are distinguished using a predetermined empirical discriminant function of slope measurements derived from normal tissue spectra and relative peak fluorescence intensity measurements in the same patient. CIN is distinguished from tissue with human papilloma virus injection or inflammation using a predetermined empirical discriminant function of average slope measurements on spectra from known normal tissue and slope measurements on a diagnostic tissue spectrum.

20 Claims, 10 Drawing Sheets

OTHER PUBLICATIONS

S. Lamb et al., "Detection and Dysplasia and Carcinoma *In Situ* by Ratio Fluorometry," *Am. Rev. Respir. Dis.*, vol. 146, pp. 1458–1461 (1992).

R. R. Alfano et al., "Optical Spectroscopic Diagnosis of Cancer in Normal Breast Tissues," *J. Opt. Soc. Am. B.*, vol. 6, pp. 1015–1023 (May 1989).

R. R. Alfano et al., "Fluoresence Spectra from Cancerous and Normal Human Breast and Lung Tissues," *IEEE Journal of Quantum Electronics*, vol. QE-23, pp. 1806–1811 (Oct. 1987).

J. Hung et al., "Autofluoresence of Normal and Malignant Bronchial Tissue," *Lasers in Surgery and Medicine*, vol. 11, pp. 99–105 (1991).

R. Richards-Kortum et al., "Spectroscopic Diagnosis of Colonic Dysplasia," *Photochemistry and Photobiology*, vol. 53, pp. 777–786 (1991).

C. Kapadia et al., "Laser-Induced Spectroscopy of Human Colonic Mucosa: Detection of Adenomatous Transformation," *Gastroenterology*, vol. 99, pp. 150–157 (1990).

P. Wong et al., "Infrared Spectroscopy of Exfoliated Human Cervical Cells: Evidence of Extensive Structural During Carcinogenesis," *Proc. Natl. Acad. Sci. USA*, vol. 88, pp. 10988–10992 (Dec. 1991).

W. Glassman, "Ultraviolet Excited Fluorescent Spectra from Non-Malignant and Malignant Tissues of the Gynecological Tract," *Lasers in the Lifesciences*, pp. 49–58 (1992).

W. Lohmann et al., "Native Fluorescence of the Cervi Uteri as a Marker for Dysplasia and Invasive Carcinoma," *European Journal of Obstetrics & Gynecology and Reproductive Biology*, vol. 31, pp. 249–253 (1989).

N. Ramanujam et al., "Diagnosis of Cervical Intraepithelial Neoplasia Using Laser-Induced Fluorescence," *Poster Presentation at Future Directions of Lasers in Surgery and Medicine III* (Mar. 1993).

DIAGNOSIS OF DYSPLASIA USING LASER INDUCED FLUOROESCENCE

BACKGROUND OF THE INVENTION

FIELD OF THE INVENTION

The invention relates to methods and apparatus to differentiate between histologically normal and histologically abnormal tissues, and to differentiate neoplastic tissue from histologically abnormal non-neoplastic tissue.

Screening for Cervical Intraepithelial Neoplasia (CIN)

Although there has been a significant decline in the incidence and mortality of invasive cervical carcinoma over the last 50 years, there has been an increase in both the reported and actual incidence of CIN. As a result, it has been estimated that the mortality of cervical carcinoma may rise by 20% in the years 2000-2004 unless screening techniques for CIN are improved.

Present screening for CIN and cervical cancer is relatively inexpensive but labor intensive because it initially relies on the results of a Pap smear; a false negative error rate of 20-30% is associated with insufficient cell sampling and/or inexpert reading of Pap smears. Given an abnormal Pap smear, colposcopic examination of the cervix (with a magnifying lens) followed by colposcopically directed biopsy and histologic examination of the tissue sample can provide a diagnosis of CIN. Histologic confirmation of the diagnosis, while relatively time-consuming and expensive, is necessary because the accuracy of classification among abnormal tissues by colposcopy alone is limited, even in experienced hands.

Improving the predictive value of colposcopy in distinguishing CIN from other abnormal tissues (e.g., tissue infected with human papilloma virus (HPV) or inflammatory tissue) could reduce the required number of biopsies and thereby increase the speed and efficiency of the screening process. Diagnosis and treatment might be combined in a single office visit, with colposcopically directed treatments including loop electrosurgical procedures (LEEP), cryo and laser therapies, and chemopreventive agents. Further, explication of improved methods to classify tissue as normal or abnormal, while not leading directly to a diagnosis of CIN, would reduce costs by allowing performance of colposcopy by medical technicians less skilled than trained colposcopists (usually physicians).

Spectroscopic Methods in Colposcopy

Spectroscopic methods for differentiating cervical neoplasia from normal cervical tissue in vivo have been described. The methods rely generally on observations that the fluorescence of abnormal tissue is significantly weaker than that of normal tissue at several excitation wavelengths, e.g., 330, 350 and 450 nm. This property has been used for spectroscopic identification of histologically abnormal tissue. For example, in vitro fluorescence intensity comparisons at an excitation wavelength of 330 nm yielded positive predictive value, sensitivity and specificity of 86%, 88% and 75% respectively on colposcopically normal and abnormal biopsies from the same patient. Differences between neoplastic (CIN) and non-neoplastic abnormal tissues (inflammation and HPV infection) yielded the largest spectroscopic differences at an excitation wavelength of 330 nm.

Additionally, fluorescence spectra have been measured in vivo to detect neoplastic tissues in different organ systems. A variety of methods for making such determinations have been proposed. For example, ratios of autofluorescence intensity at two different emission wavelengths have been used by many groups, and scores based on multi-variate linear or non-linear regressions and fits to extract concentrations of various chromophores have been proposed by many others for inclusion in decision criteria.

In one application, 337 nm wavelength excitation was applied to colonic tissue. Multi-variate linear regression analysis was used to correctly distinguish adenomatous polyps from normal colon and hyperplastic polyps with positive predictive value, sensitivity and specificity of 86%, 86% and 80% respectively.

Tissue Classification Methods

Previous attempts to reliably distinguish CIN from inflammation or HPV infection in vivo using colposcopy alone have been unsuccessful. Fluorescence intensity may be useful in this regard, but is not sufficient in itself because analogous fluorescence intensity measurements of the same tissue type may vary by more than a factor of two from patient to patient, and by about 15% within the same patient. Methods relating fluorescence intensities from abnormal and normal tissues of the same patient, however, tend to be more predictable and therefore more diagnostically useful.

Thus, in general, each patient must serve as her own control. Considering cervical tissues in a given patient excited with 337 nm wavelength electromagnetic excitation, tissues with HPV infection are less fluorescent with than tissues with chronic inflammation, and tissues with dysplastic changes exhibit even lower fluorescence than those with HPV infection. The lowest level of fluorescence (relative to analogous fluorescence measurements on other tissue types in the same patient) is exhibited by tissues with the most abnormal form of CIN. Analogous relationships among tissue fluorescence intensity measurements in a patient may exist if excitation wavelengths other than 337 nm are used because the shape and intensity of cervical tissue spectra do not change substantially when the excitation wavelength is increased or decreased by less than 10 nm.

Additional information useful for tissue classification may be found in the peak emission wavelength of tissues with CIN, which is positively correlated with the peak emission wavelengths of normal tissue spectra from the same patient. This relationship, however, is not observed for tissue samples with inflammation or HPV infection.

Thus, a reliable method to spectroscopically classify tissue as normal or abnormal, and in the latter case to distinguish inflammation or HPV infection from CIN, is needed. Such a method could rely on one or more of the relationships described above, augmented with additional information indicative of the particular separation or classification desired.

SUMMARY OF THE INVENTION

The present invention includes in vivo spectroscopic methods and apparatus for differentiating normal tissue from abnormal tissue and for diagnosing CIN in diagnostic cervical tissue samples. Diagnostic cervical tissue samples are the tissue samples to be evaluated by the non-invasive methods of the present invention. The methods include analysis of tissue fluorescence intensity spectra or portions thereof from both histologically normal tissue and histologically abnormal tissue in a patient desiring diagnosis.

Reference in this application to histologically normal cervical tissue samples in a patient subject to the diagnostic methods of the present invention refers to tissue which is presumptively histologically normal. Normal tissue samples in such subjects are selected in vivo and tested non-invasively as described herein to ensure a substantial likelihood that they actually represent tissue which, if histologically evaluated, would be classified normal.

In certain preferred embodiments, the spectra are represented on two-dimensional plots with fluorescence intensity being represented on the vertical axis and wavelength on the horizontal axis. For calculations involving slope measurements at predetermined wavelengths within spectra having different (unnormalized) peak values, each spectrum is normalized to its own maximum intensity value. For calculations involving the ratio of the peak intensity of a spectrum from unknown tissue (i.e., from a diagnostic cervical tissue sample) to the peak intensity of a spectrum from (presumptively) normal tissue in the same patient, normalization is not performed.

Detecting Tissue Abnormality

According to the present invention, an in vivo method of detecting tissue abnormality in a diagnostic cervical tissue sample in a patient having known normal cervical tissue comprises illuminating the diagnostic tissue sample and normal cervical tissue with electromagnetic radiation (preferably about 337 nm wavelength). A plurality of normal fluorescence intensity spectra are detected from the known normal cervical tissue, the spectra being obtained serially or simultaneously, preferably through fiber optics which may be placed at a fixed distance from the cervical tissue. In some embodiments, spectra may be detected through analysis of a cervical image which includes the tissue areas to be sampled.

A peak normal fluorescence intensity value is measured in each said normal fluorescence intensity spectrum, and an average peak normal fluorescence intensity calculated from said peak normal fluorescence intensity values. A fluorescence intensity spectrum is also detected from the diagnostic tissue sample, and a peak fluorescence intensity value measured from said fluorescence intensity spectrum.

A predetermined portion of the fluorescence intensity spectrum (preferably in the region corresponding to wavelengths between about 410 nm and about 430 nm) from the diagnostic tissue sample furnishes slope information for calculation of a slope parameter which is indicative of tissue abnormality. The predetermined portion is empirically identified in prior clinical trials as facilitating accurate classification of tissue, and the slope parameter is preferably a function of average slope in the predetermined portion. Each spectrum is preferably normalized to its own maximum value prior to calculation of the slope parameter.

Relative peak fluorescence intensity (preferably relative to average peak normal fluorescence intensity) is calculated as a function of said peak fluorescence intensity value, and tissue abnormality is detected as a function of the calculated slope parameter and relative peak fluorescence intensity. The latter function is preferably a predetermined empirical discriminant function obtained from prior clinical trials. The discriminant function may be either linear or nonlinear.

Detecting CIN

According to the present invention, an in vivo method of detecting CIN in a diagnostic cervical tissue sample in a patient having known normal cervical tissue comprises classifying the diagnostic cervical tissue sample as abnormal by a method described herein, followed by illumination of the diagnostic tissue sample and known normal cervical tissue with electromagnetic radiation, preferably of about 337 nm wavelength.

A first fluorescence intensity spectrum from the diagnostic tissue sample is detected, as is a second fluorescence intensity spectrum from the known normal cervical tissue. A first slope parameter which is indicative of CIN in the diagnostic cervical tissue sample is calculated from a predetermined portion of said first fluorescence intensity spectrum (corresponding to wavelengths between about 440 nm and about 460 nm). A second slope parameter which characterizes normal cervical tissue in the patient is calculated from a predetermined portion of said second fluorescence intensity spectrum (corresponding to wavelengths between about 410 nm and about 430 nm). Both first and second slope parameters are preferably calculated after normalization of the respective fluorescence intensity spectra to peak fluorescence intensity values of 1. Additionally, both first and second slope parameters are preferably functions of average slopes in said normalized first and second fluorescence intensity spectra respectively in regions lying substantially between wavelengths correcponding to the respective predetermined portions.

CIN is detected in the diagnostic cervical tissue sample as a function of said first and second slope parameters, the function preferably comprising a predetermined empirical discriminant function which, in some preferred embodiments is linear.

DETAILED DESCRIPTION

Figure 1:
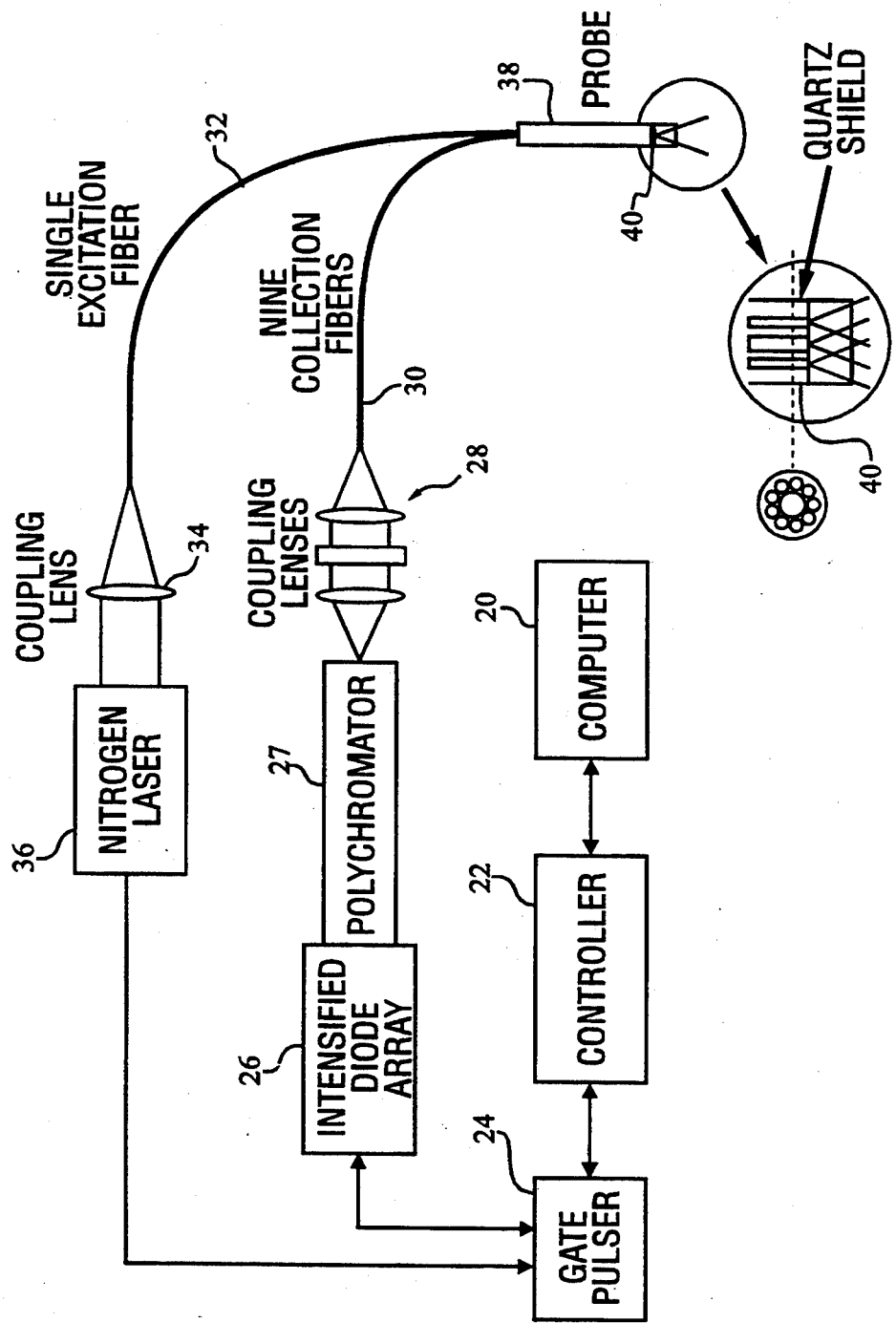
FIG. 1 is a schematic representation of apparatus to classify cervical tissue according to the present invention.

CIN—cervical intraepithelial neoplasia
HPV—human papilloma virus

Normal/Abnormal Tissue Classification

Normal/abnormal tissue classification requires induced fluorescence intensity spectra from tissue areas known to be normal with a sufficiently high probability of accurate classification. Normal and abnormal cervical tissues are primarily identified in vivo by colposcopists. In any given patient, it is preferable to collect a plurality of fluorescence intensity spectra from tissue areas identified as normal by a colposcopist. An expected error rate of about 10–20% has been observed, which primarily represents samples which are colposcopically normal but in fact comprise inflammatory tissue. As explained below, provision is made for removal of erroneously-identified normal samples, with the result that those remaining are presumptively normal.

As a patient is examined, peak normal fluorescence intensity values are measured on each spectrum from normal tissue. The intensity values are averaged and a standard deviation of normal peak values calculated. Depending on the degree of confidence required in the screening results and the skill of the operators, a portion of all spectra initially identified as colposcopically normal are discarded (i.e., the spectra are not included in calculation of the average peak normal fluorescence intensity, but may be assigned to the group of spectra to be classified subsequently as normal or abnormal). Criteria for discarding colposcopically normal samples may preferably require discarding all spectra associated with peak values which fall more than one standard deviation below the average peak normal fluorescence intensity.

The peak fluorescence intensity of any test fluorescence spectrum (associated with cervical tissue to be evaluated for normality/abnormality) is divided by the corresponding average normal fluorescence intensity for that patient to yield a relative peak fluorescence intensity for that spectrum. Because normal tissue tends to have relatively high and uniform peak fluorescence intensities in any given patient, the above division will generally result in relative peak fluorescent intensities clustered around a value of approximately 1 for normal tissues. On the other hand, because abnormal tissue (whether characterized as inflammation, HPV infection, or CIN) tends to have lower-than-normal peak fluorescence intensities, the above division will generally result in relative peak fluorescent intensities clustered around a value substantially less than 1 for abnormal tissues. This condition furnishes a partial basis for classifying spectra as representing either normal or abnormal tissue.

A more complete basis for identification of spectra as representing either normal or abnormal tissue is provided by examination of a slope parameter associated with each spectrum, the parameter preferably being derived from slopes measured in the range 400–440 nm, preferably 410–430 nm, and in some preferred embodiments 415–425 nm, as measured on a spectrum normalized to its own peak fluorescence value. The measured slope value is largely governed by two factors, i.e., the peak emission wavelength of fluorophores contributing to the spectrum, and the reabsorption effect of oxyhemoglobin with an absorption peak at 420 nm. As more hemoglobin contributes, the peak shifts to longer wavelengths and the slope increases. Similarly, as more NADH fluorescence contributes, the peak shifts to longer wavelengths and the slope increases. These effects are observed in diseased tissue, and probably account in part for the capacity of methods of the present invention to differentiate types of diseased tissue on the basis of their induced fluorescence spectra.

The parameter may be an average or tangential slope or other representative value of the range of actual slope values which will in general be found within the specified range (predetermined portion) in any normalized spectrum. Wavelengths defining the extent and location of the predetermined portion of a normalized spectrum which is indicative of tissue abnormality are determined from clinical trials involving fluorescence spectra obtained from tissue with histologically proven diagnoses. That is, the definition of the predetermined portion is empirically derived by comparing slopes over the entire wavelength range to find the portion of that range yielding the best discrimination using the methods described above.

Figure 4:
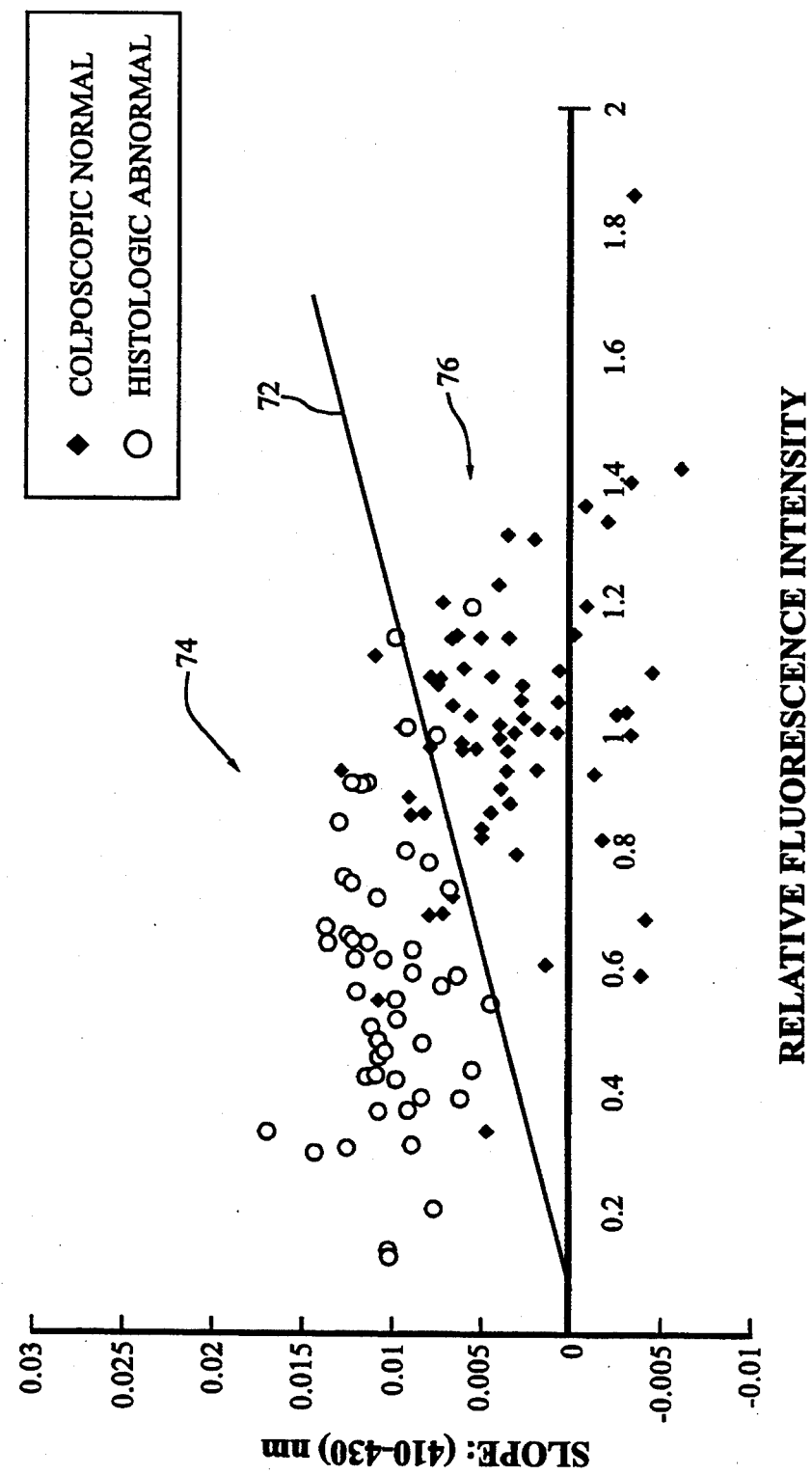
FIG. 4 represents a population of induced fluorescence intensity spectra representing colposcopically normal and histologically abnormal tissue, with a discriminant function for detecting tissue abnormality.

To evaluate a diagnostic cervical tissue sample, a relative peak fluorescence intensity and a slope parameter are calculated as explained above from its induced fluorescence intensity spectrum. The calculated values may then be plotted as a point on the graph of FIG. 4. The line 72 represents a predetermined empirical discriminant function which substantially separates points characterizing colposcopically normal and histologically abnormal tissue. If the point falls below line 72, the tissue sample is diagnosed as normal, whereas if the point falls above line 72, the tissue sample is diagnosed as abnormal. These decision criteria may be implemented mathematically as well as graphically by considering the equation of the line which can be derived from FIG. 4. Note that the position of line 72 (slope and intercept) are subject to change with the addition of more data points from clinical trials to those already present on FIG. 4. Note also, that the position of line 72 may also be expected to change when populations having a substantially different incidence of abnormal cervical tissue from that illustrated in FIG. 4 are considered.

Differentiating CIN From Other Abnormal Tissues

Although normal/abnormal tissue classification on the basis of induced fluorescence spectra is useful for preliminary screening, patients identified as having abnormal cervical tissue must be further evaluated. In particular, CIN should be differentiated from inflammation or HPV infection because of the potential for CIN to progress to invasive cancer.

As an aid to classification, a correlation has been observed between the wavelengths associated with peak intensity in corresponding fluorescence intensity spectra obtained from normal and neoplastic tissue in the same patient. Whereas three sample peak intensity wavelengths of normal spectra in a single patient were observed to be 398, 426 or 442 nm, the corresponding peak intensity wavelengths from CIN spectra in the same patient were observed to be 442, 450 or 460, respectively. Thus, the peak intensity of a fluorescence intensity spectrum tends to occur at longer wavelengths in fluorescence intensity spectra from tissue with CIN, compared to corresponding spectra from normal tissue in the same patient. This wavelength shift is relatively uncommon in abnormal tissues representing HPV infection or inflammation.

Figure 5:
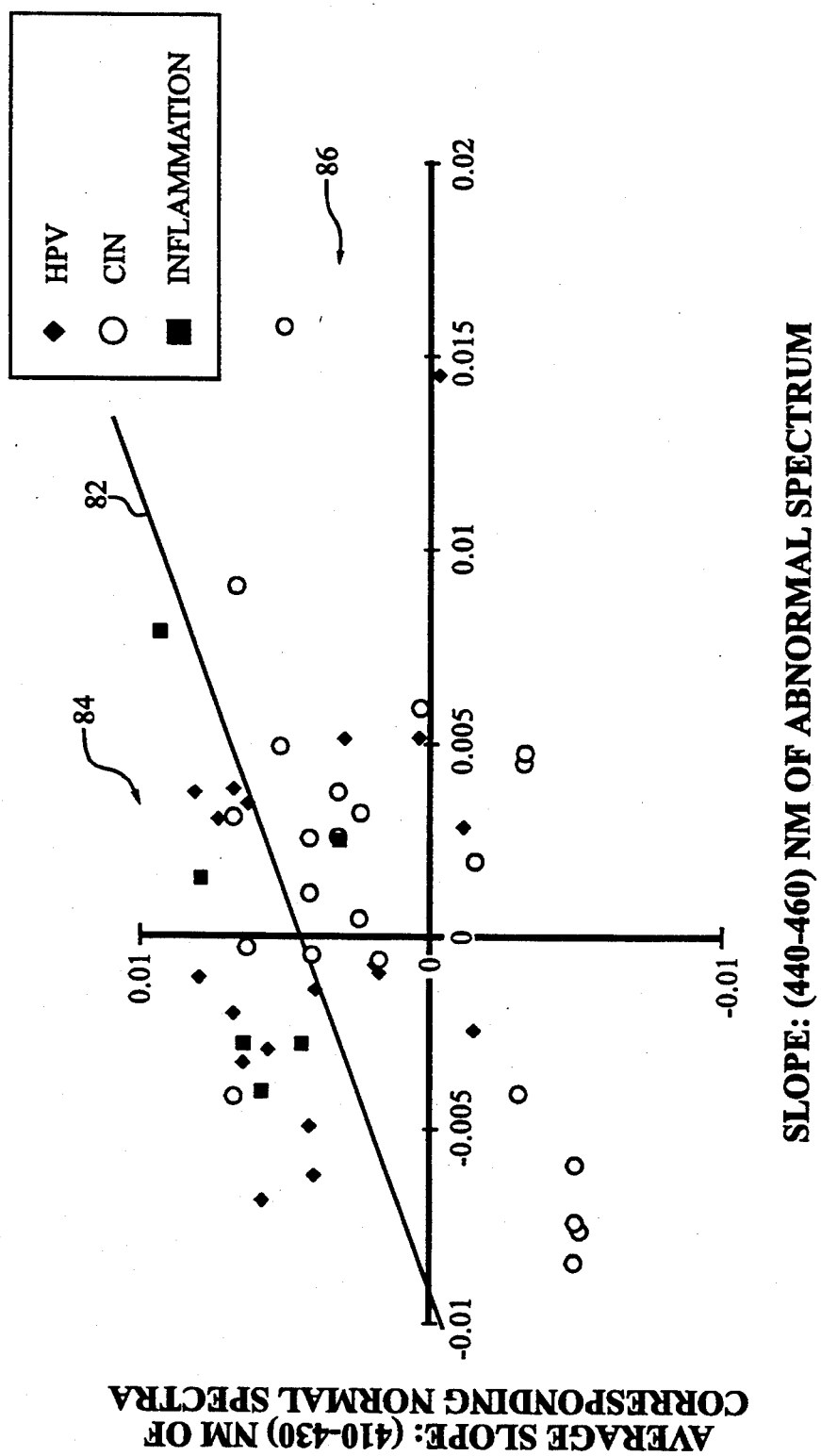
FIG. 5 represents a population of induced fluorescence intensity spectra representing histologically abnormal tissue (i.e., CIN, inflammation, HPV), with a discriminant function for detecting CIN.

A two-dimensional scatter plot was developed to map out the relationship in a population of patients between the peak emission wavelength of the abnormal spectrum and average normal spectra from the same patient. This is shown in FIG. 5, where the abscissa corresponds to the slope of the abnormal spectrum over the wavelength range 440 to 460 nm, and the ordinate represents the average slope of the normal spectra from the same patient over the wavelength range 410–430 nm. All spectra were normalized to a peak intensity of 1 prior to slope calculation. Note that the slope of the spectra from samples with HPV infection or inflammation does not appear to correlate to the average slope of the corresponding normal spectra (linear correlation coefficient=0.072). However, the slope of the spectra from samples with CIN displays a positive correlation (linear correlation coefficient=0.442) to the average slope of the corresponding normal spectra. This enables differentiation of abnormal samples with CIN from those with HPV infection or inflammation. A predetermined empirical discriminant function which allows one to carry out the differentiation for each new patient is represented by the line 82 in FIG. 5, which minimizes the number of misclassified samples.

Thus, CIN tissue spectra are distinguishable from HPV or inflammation tissue spectra on a two-dimensional plot. The horizontal axis of the plot represents the value of a slope parameter obtained from an abnormal spectrum in the wavelength range of about 440 to 460 nm, while the vertical axis represents the value of a slope parameter obtained from a normal spectrum in the same patient in the wavelength range of about 410 to 430 nm.

A predetermined empirical function in two-dimensional space substantially separates points corresponding to CIN tissue fluorescence spectra from points corresponding to HPV or inflammation tissue spectra. In certain preferred embodiments, this function may be linear and acceptably minimize the number of misclassified points. In other preferred embodiments, the function may describe a nonlinear decision surface. Determination of the preferred decision surface for any population depends on the degree to which the population is characterized by clinical data used to estimate the decision surface.

Apparatus for tissue classification

FIG. 1 is a schematic representation of apparatus to classify cervical tissue according to the present invention. To obtain tissue fluorescence spectra, electromagnetic radiation (e.g., light, in certain embodiments) in the form of laser light from nitrogen laser 36 is applied through coupling lens 34 and single fiber optic excitation fiber 32 to probe 38. Also within probe 38 are collection fiber optic fibers 30 and quartz shield 40, the shield 40 acting to keep fibers 30 and 32 properly spaced from any surface to which probe 40 is applied, application to a cervix preferably being under colposcopic observation. Resulting tissue fluorescence is transmitted by fibers 30 through coupling lenses 28 to polychromator 27, and thence to intensified diode array 26. Array 26, controlled by controller 22 through gate pulser 24, detects fluorescence intensity spectra which are relayed through controller 22 to computer 20. Computer 20 is programmed to classify tissue in accordance with methods described herein.

Note that laser light is not necessary for practice of the present invention. Laser 36 may be replaced in some embodiments by an incandescent or other type lamp with an associated filter to produce quasi-monochromatic light. Additionally, fibers 32 and 30 may be replaced in some embodiments with fibers serving both the function of illumination (excitation) and transmission of tissue fluorescence. Intensified diode array 26 and polychromator 27 may be replaced by a subassembly comprising radiation filters and photomultiplier tubes to reduce costs in certain embodiments.

Figure 2:
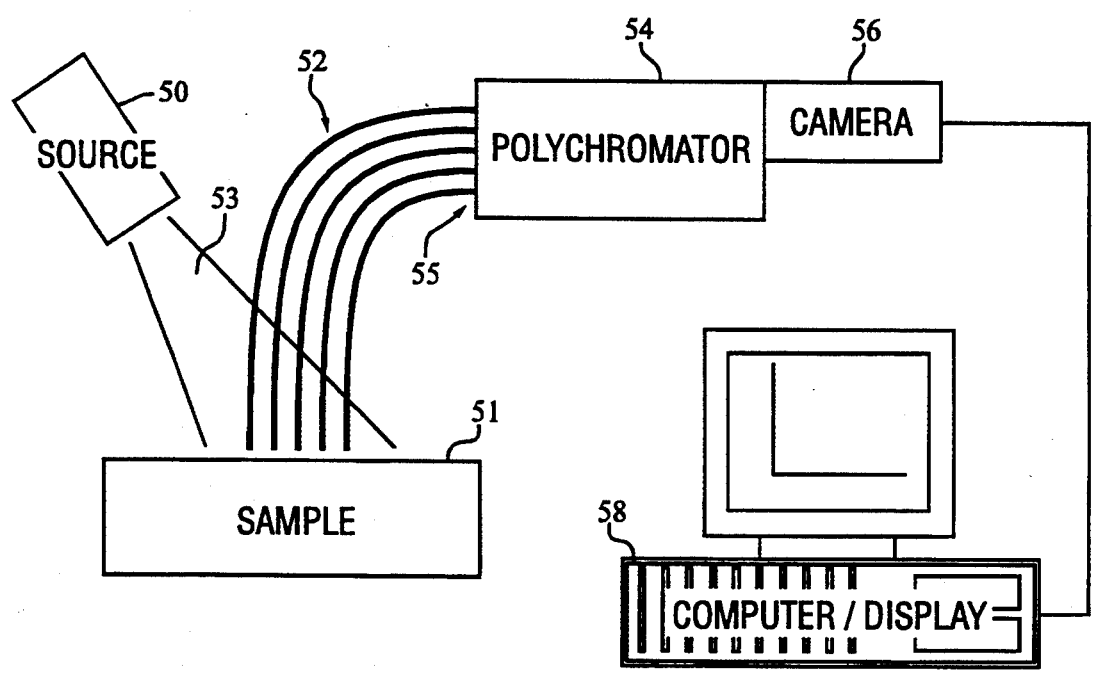
FIG. 2 is a schematic representation of apparatus for multi-pixel spatial-spectral imaging of the cervix.

FIG. 2 schematically illustrates apparatus used in certain embodiments of the present invention to simultaneously collect fluorescence spectra from multiple areas of the cervix. A source 50 of electromagnetic radiation (delivered through fiber or non-fiber optics) is used to illuminate the desired areas of the cervix (sample 51), including both some normal and some abnormal areas. A geometric array 53 of fibers 52 collects tissue fluorescence originating from known normal and unknown regions of the cervix, the latter to be diagnosed. The ends of fibers 52 proximate to imaging polychromator 54 are arranged in a linear array 55 at the entrance slit to polychromator 54. Polychromator 54 is coupled to a charge coupled device camera 56. Polychromator 54 disperses wavelength across one axis of the array, and position on the cervix varies across the other dimension. Thus this system provides a spatial-spectral image on computer-display 58 of fluorescence spectroscopic information in the cervix.

The operator identifies one or more fibers which view normal cervix. The fluorescence intensity spectrum from each fiber viewing an unknown area of the cervix is then processed by the methods described herein to determine whether the tissue is histologically abnormal and whether CIN is present. This information can be presented as a spatial image of tissue histologic condition on computer-display 58.

Figure 3:
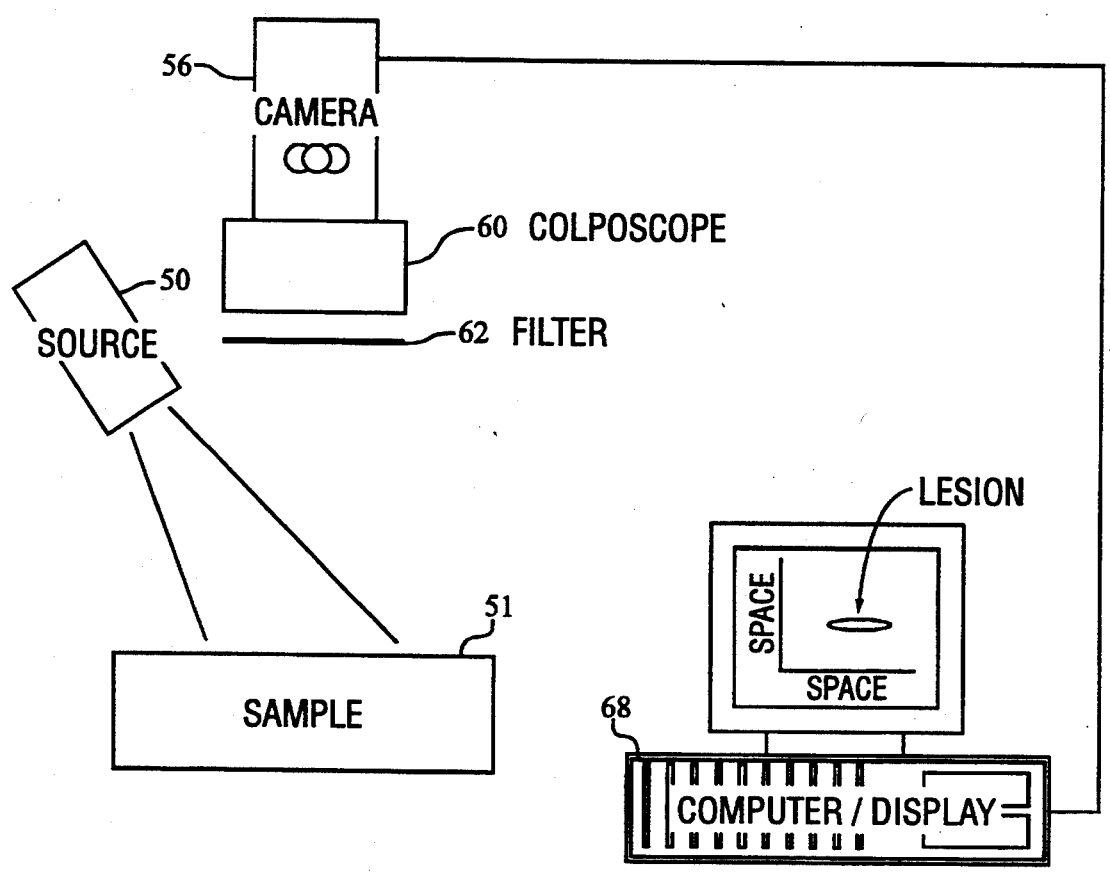
FIG. 3 is a schematic representation of apparatus to acquire and process spectroscopic images of the cervix.

FIG. 3 is a schematic illustration of apparatus for certain embodiments of the present invention. As in FIG. 2, illumination of sample 51 with electromagnetic radiation from source 50 results in fluorescence intensity spectra which are sensed by charge coupled device 56 after passing through variable band pass filter 62 and colposcope imaging optics 60. Computer/display unit 68 accepts spectra from charge coupled device 56 for processing and display.

This system provides a two-dimensional image of variation in fluorescence intensity as a function of position on the cervix at a specific wavelength band governed by the transmission characteristics (optical properties) of imaging optics 60 and filter 62, which can be rapidly changed. Images are acquired at bands centered near 398, 410, 426, 442, 450 and 460 nm sequentially. The maximum intensity $I_{MAX}$ is identified for each pixel. A composite image indicating the peak intensity as a function of position is then formed from these images. Images indicating the slopes of the fluorescence spectra from the tissue in each pixel over the ranges 410–430 nm and 440–460 nm are calculated according to $I(426)-I(410)/[(426-410)I_{MAX}]$ and $I(460) - I(442)/[(460-442)I_{MAX}]$. The operator identifies one or more pixels corresponding to normal regions of the cervix. A relative intensity image is constructed by dividing the peak intensity image by the average normal intensity. Thus, for each pixel the relative intensity and slopes at 410–430 nm and 440–460 nm are available. These data are used to classify the state of the tissue in each pixel according to the methods presented herein. This information can be presented on computer-display unit 68 as a spatial image of tissue histologic condition.

Obtaining Decision Surfaces

Data points in FIG. 4 represent induced fluorescence intensity spectra obtained from cervical tissue in a population of patients, each patient having both colposcopically normal tissue and histologically abnormal tissue. The latter tissue includes CIN, inflammatory tissue, and tissue having HPV infection. Note that fluorescence intensities plotted along the abscissa of FIG. 4 are relative to (divided by) average peak normal fluorescence intensity obtained from the population of spectra considered. Spectra from the two tissue groups are processed in accordance with methods described herein to classify the respective tissues as normal or abnormal. Decision surface 72 (a line in 2-space) is empirically established to minimize overlap of substantially normal 76 and substantially abnormal 74 groups. The equation of surface 72 as determined from FIG. 4 constitutes a predetermined discriminant function useful in detecting tissue abnormality in any diagnostic cervical tissue sample when fluorescence intensity spectra are induced in the tissue sample and processed according to methods described herein.

Data points in FIG. 5 represent induced fluorescence intensity spectra obtained from cervical tissue in a population containing histologically abnormal tissue, the latter tissue including CIN, inflammatory tissue, and tissue having HPV infection. Spectra from the three tissue groups are processed in accordance with methods described herein to classify the respective tissues as characteristic of CIN or not characteristic of CIN. Decision surface 82 (a line in 2-space) is empirically established to minimize overlap of substantially CIN 86 and substantially not-CIN 84 groups. The equation of surface 82 as determined from FIG. 5 constitutes a predetermined discriminant function useful in detecting CIN in any histologically abnormal diagnostic cervical tissue sample when fluorescence intensity spectra are induced in the tissue sample and processed according to methods described herein.

Figure 6A:
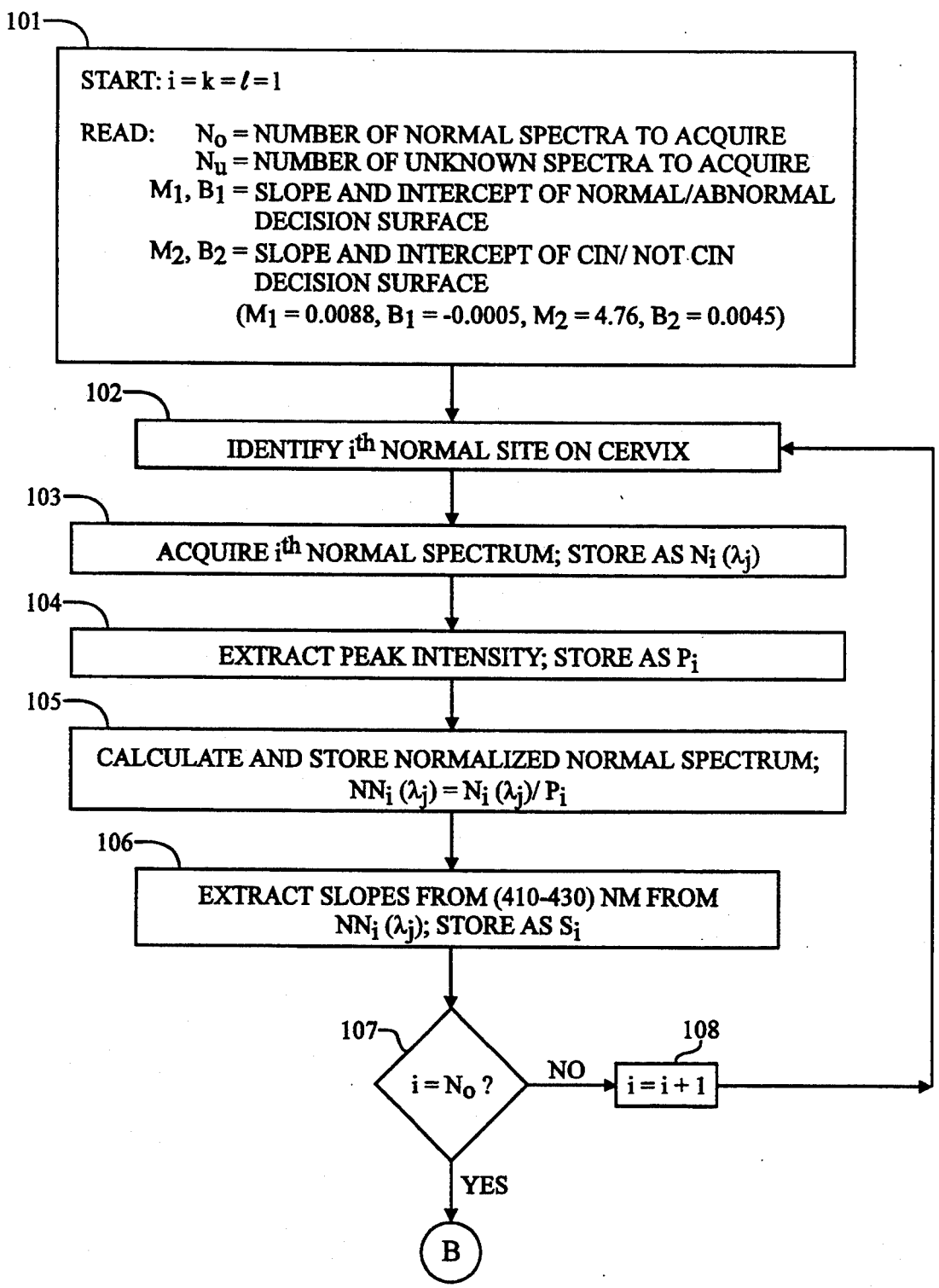
FIGS. 6A–6F illustrate a flow chart to practice preferred embodiments of the methods of the present invention.
Figure 6B:
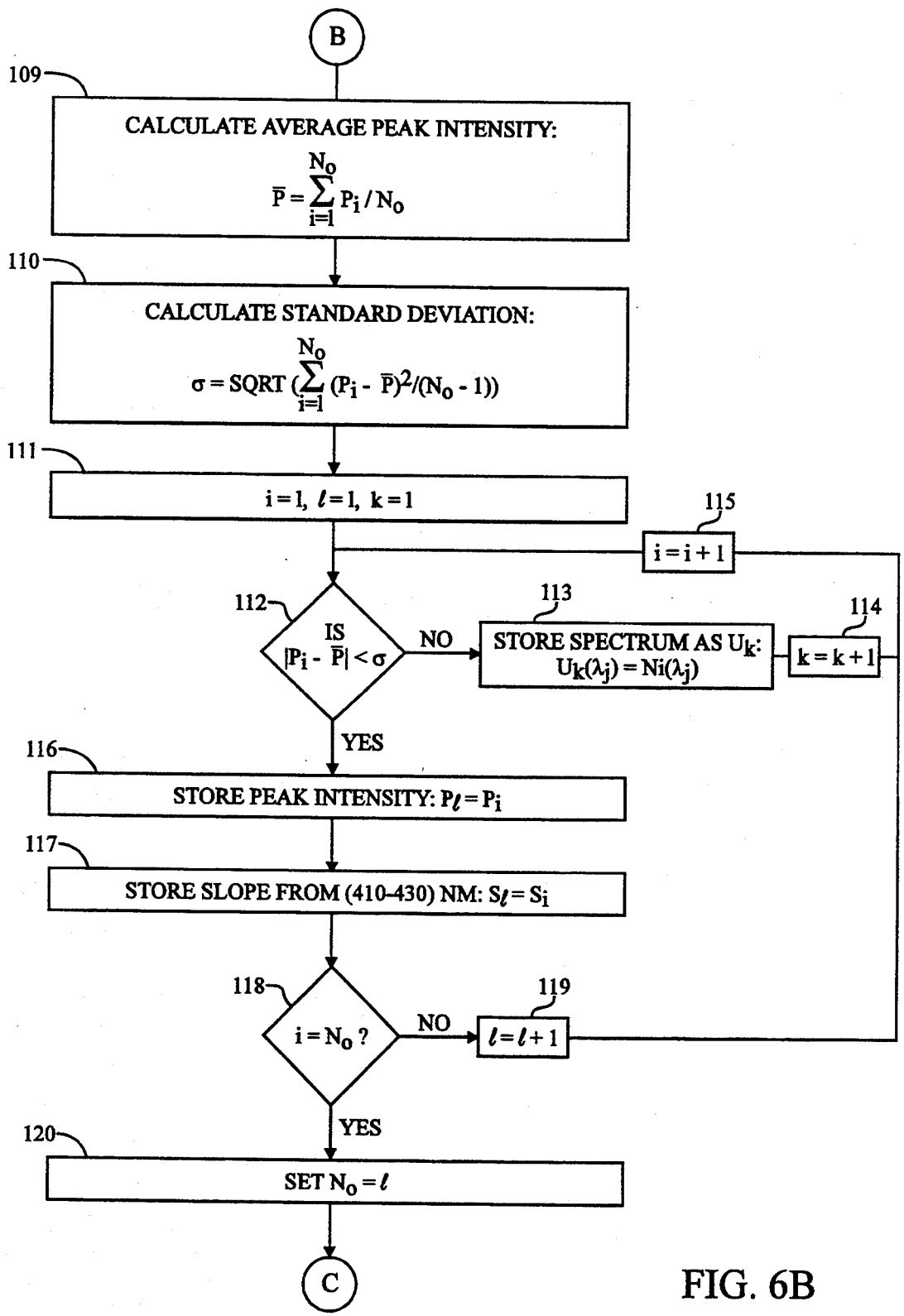
Figure 6C:
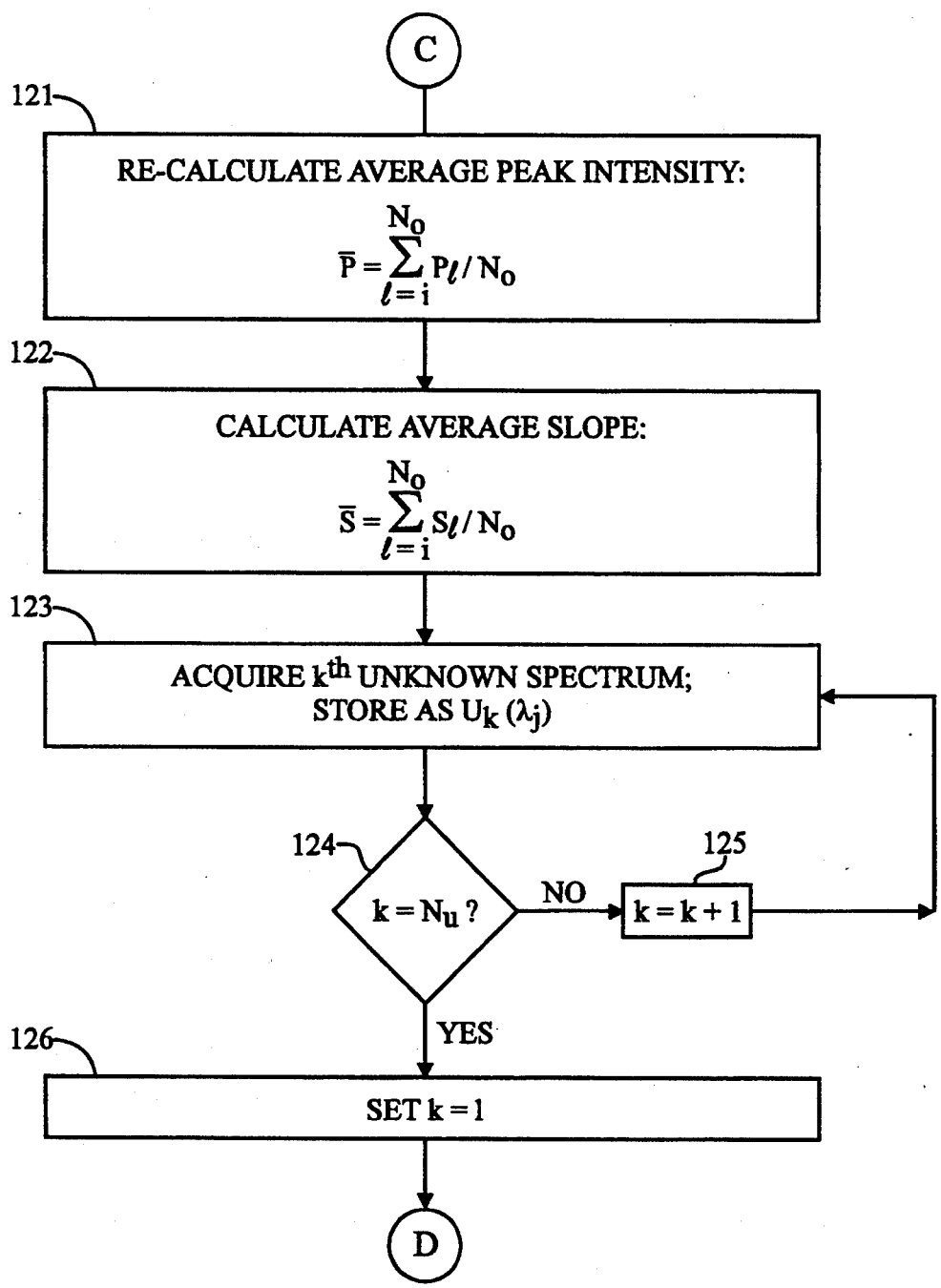
Figure 6D:
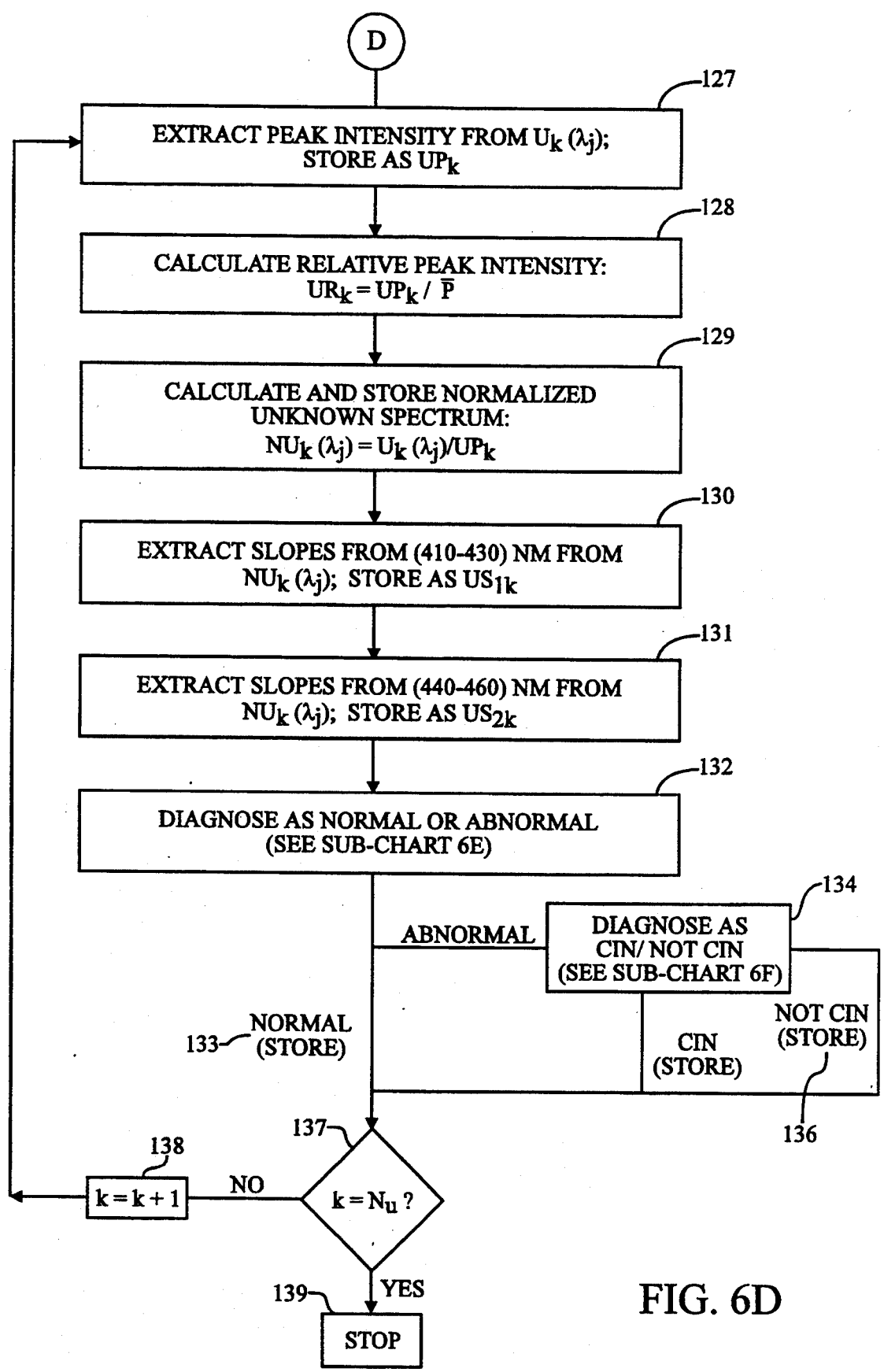
Figure 6E:
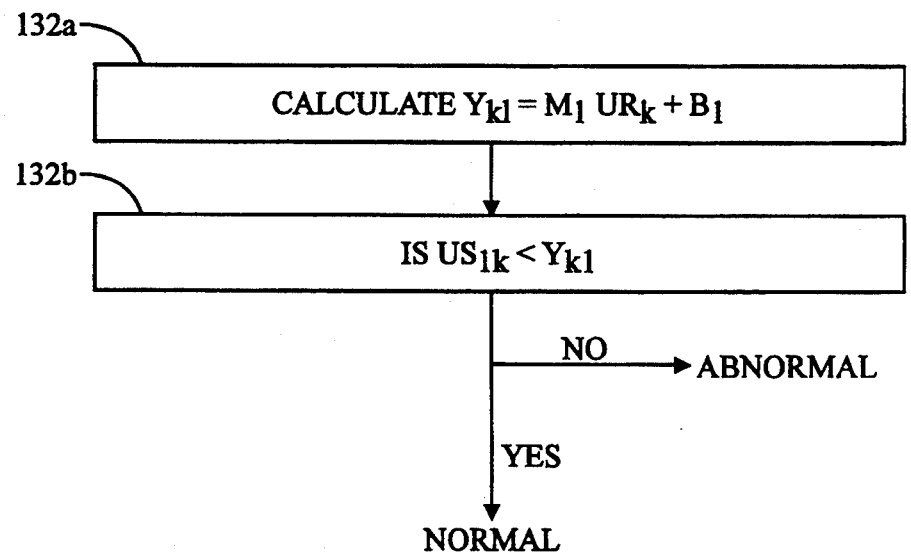
Figure 6F:
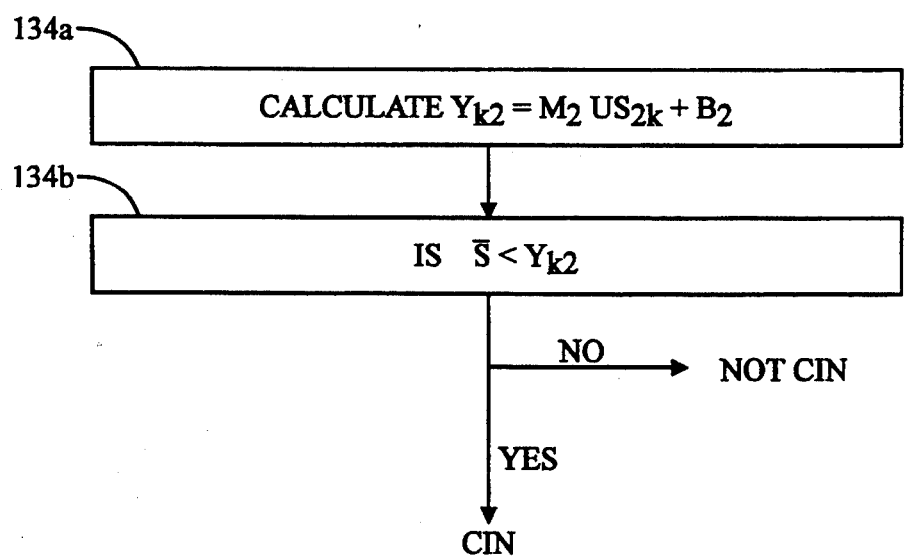

FIGS. 6A-6F illustrate a flow chart to practice preferred embodiments of the methods of the present invention. Note that steps in the flow chart continue from FIG. 6A to FIG. 6B, from FIG. 6B to FIG. 6C, and from FIG. 6C to FIG. 6D. FIGS. 6E and 6F represent subroutines to apply the particular decision rules applicable to either separation of tissue into normal and abnormal classifications (FIG. 6E), or identification of CIN in samples of abnormal tissue (which may include CIN, inflammation or HPV infection) (FIG. 6F). The subroutines (subcharts) illustrated in FIGS. 6E and 6F are called for within the steps illustrated in FIG. 6D. It is assumed in applying the steps called for in FIGS. 6A-6F that sufficient spectra are made available to ensure that normal cervical tissue in the patient is identified and characterized by fluorescence spectra with a sufficiently high likelihood of accurate classification, as indicated in the methods described herein.

Referring to FIGS. 6A-6F, the process steps executed in the diagnostic method of the present invention are shown. After the method is started, the following parameters are initialized in step 101:

counters i, k, l are initialized to 1;
$N_o$—the number of normal spectra to acquire;
$N_u$—the number of unknown spectra to acquire;
$M_1$—the slope of the normal/abnormal decision surface=0.0088;
$B_1$—the intercept of the normal abnormal decision surface=0.0005;
$M_2$—the slope of the CIN/not CIN decision surface=4.76;
$B_2$—the intercept of the CIN/not CIN decision surface=0.0045.

In step 102, the operator identifies the ith normal site on the cervix. The ith normal spectrum is acquired and stored in memory as $N_i(\lambda_j)$ in step 103. In step 104, the largest (peak) intensity value is extracted from $N_i(\lambda_j)$; this value is stored in memory as $P_i$. In step 105, the normalized normal spectrum from site i ($NN_i(\lambda_j)$) is calculated as $NN_i(\lambda_j)=N_i(\lambda_j)/P_i$ and stored in memory. In step 106, the slope of the spectrum from 410–430 nm, $S_i$, is calculated from $NN_i(\lambda_j)$ as $S_i=[NN_i(430)-NN_i(410)]/(430 \text{ nm}-410 \text{ nm})$. This value is stored in memory in step 106.

In step 107 the value of i is compared to $N_o$. If i≠$N_o$, then i is reset to i+1 in step 108 and the method returns to step 102. Steps 102 through 107 are repeated until counter i is equal to $N_o$. At this time, step 109 is executed, wherein the average peak intensity of normal spectra, $\bar{P}$, is calculated as $$\bar{P} = \sum_{i=1}^{N_o} P_i/N_o$$

and stored in memory. Step 110 is then executed in which the standard deviation of the peak intensity, $\sigma$, is calculated as $$\sigma = \sqrt{\sum_{i=1}^{N_o} (P_i - \bar{P})^2/(N_o - 1)} \ .$$

This value is stored in memory and then block 111 is executed wherein counters i, l and k are reset to 1.

Blocks 112 through 122 determine which of the spectra collected from areas identified as normal will be considered normal within the method and which will later be reclassified as normal or abnormal in later steps of the method. In block 112, the values of $P_i$ and $\bar{P}$ are compared. If $P_i-\bar{P}$ is greater than $\sigma$ the spectrum from the ith sample ($N_i(\lambda_j)$) is renamed and stored in memory as $U_k(\lambda_j)$ in block 113. The type of this sample is classified later within the method. Following this, blocks 114 and 115 are executed where the counters k and i are incremented by one respectively. Control is then returned to block 112 of the method. If $P_i-\bar{P}$ is not greater than $\sigma$, the peak intensity of the corresponding spectrum ($P_i$) is renamed and stored as $P_l$ in block 116. In block 117, executed next, the slope of the spectrum from 410–430 nm ($S_i$) is renamed and stored as $S_l$. The type of this sample is considered normal within the method. In block 118 the method tests to see whether i=$N_o$. If not, in block 119, the counter l is incremented by one and in block 115 the counter i is incremented by one. Control is returned to block 112 and the sequence from 112 to 118 is repeated until all acquired spectra have been tested and i is equal to $N_o$. At this time, control is shifted to block 120 and $N_o$ is reset to l and stored in memory.

In block 121, the average peak intensity of those samples considered normal is recalculated ($\bar{P}$) and stored according to $$\bar{P} = \sum_{l=1}^{N_o} P_l/N_o$$

In block 122 the average slope of those samples considered normal ($\bar{S}$) is calculated and stored in memory according to $$\bar{S} = \sum_{l=1}^{N_o} S_l/N_o.$$

In block 123, the operator is directed to acquire the kth unknown spectrum, $U_k(\lambda_j)$; this is stored in memory. In block 124 it is determined whether the desired number of unknown spectra, $N_u$, have been collected by testing whether $k=N_u$. If not, in block 125 k is incremented by one and control is returned to block 123. The steps in blocks 123 to 124 are repeated until $k=N_u$, at which time, control is shifted to block 126 and k is reinitialized to 1.

Control is then passed to block 127, where the peak intensity is extracted from the kth unknown spectrum, $U_k(\lambda_j)$, and stored as $UP_k$. The relative peak intensity of the kth unknown spectrum, $UR_k$, is then calculated as $UR_k = UP_k/\overline{P}$ in block 128 and stored. The normalized unknown spectrum, $NU_k(\lambda_j)$ is then calculated as $NU_k(\lambda_j) = U_k(\lambda_j)/UP_k$ and stored in block 129. In block 130, the slope of the kth normalized unknown spectrum from 410–430 nm ($US_{1k}$) is calculated as $US_{1k} = (NU_k(430 \text{ nm}) - NU_k(410 \text{ nm}))/(430 \text{ nm} - 410 \text{ nm})$ and stored.

In block 132 the type of the kth unknown sample is determined as normal or abnormal by following the steps in FIG. 6E. In block 132a, the parameter $Y_{k1}$ is calculated for the kth unknown spectrum as $Y_{k1} = M_1 UR_k + B_1$; this value is stored in memory. In block 132b, $US_{1k}$ is compared to $Y_{k1}$. If $US_{1k}$ is less than $Y_{k1}$, the sample is classified as normal; this information is stored in memory in block 133 and control is transferred to block 137. If $US_{1k}$ is not less than $Y_{k1}$, the sample is classified as abnormal and control is passed to block 134. In block 134, the steps of FIG. 6F are used to diagnose whether or not the abnormal sample contains CIN. In block 134a, the parameter $Y_{k2}$ is calculated for the kth unknown spectrum as $Y_{k2} = M_2 US_{2k} + B_2$. This value is stored in memory. In block 134b, the values of S and $Y_{k2}$ are compared. If S is less than $Y_{k2}$ then the sample is classified as CIN and this information is stored in memory in block 135. If S is not less than $Y_{k2}$ then the sample is classified as abnormal, but not containing CIN, and this information is stored in memory in block 136. When the sample type of the kth unknown sample has been classified, in blocks 133, 135 or 136, control is passed to block 137, where the values of k and $N_u$ are compared. If k is not equal to $N_u$, the counter k is incremented by one in block 138 and control returns to block 127. The steps in blocks 127 through 137 are repeated until k is equal to $N_u$, indicating that all unknown samples have been classified and the method is stopped in block 139.

What is claimed is:

1. An in vivo method of detecting tissue abnormality in a diagnostic cervical tissue sample in a patient, comprising:
   illuminating the diagnostic cervical tissue sample and a presumptively histologically normal cervical tissue sample with electromagnetic radiation;
   detecting a first fluorescence intensity spectrum from the diagnostic tissue sample;
   detecting a second fluorescence intensity spectrum from the presumptively histologically normal cervical tissue sample;
   calculating from a predetermined portion of said first fluorescence intensity spectrum, a first slope parameter which is indicative of tissue abnormality;
   calculating from a predetermined portion of said second fluorescence intensity spectrum, a second slope parameter which is indicative of presumptively histologically normal cervical tissue; and
   detecting tissue abnormality in the diagnostic cervical tissue sample as a function of said first and second slope parameters.

2. The method of claim 1, said illuminating step comprising, illuminating said diagnostic cervical tissue sample and said presumptively histologically normal cervical tissue sample with electromagnetic radiation having a wavelength of about 337 nm.

3. The method of claim 1, said step of calculating said first slope parameter comprising, calculating said first slope parameter from a portion of said first fluorescence intensity spectrum corresponding to wavelengths between about 440 nm and about 460 nm.

4. The method of claim 1, said step of calculating said second slope parameter comprising, calculating said second slope parameter from a portion of said second fluorescence intensity spectrum corresponding to wavelengths between about 410 nm and about 430 nm.

5. The method of claim 1, said step of calculating said first slope parameter comprising, calculating said first slope parameter after normalization of said first fluorescence intensity spectrum with a peak fluorescence intensity value of said first fluorescence intensity spectrum.

6. The method of claim 5, wherein said first slope parameter is a function of an average slope in said predetermined portion of said normalized first fluorescence intensity spectrum.

7. The method of claim 1, said step of calculating said second slope parameter comprising, calculating said second slope parameter after normalization of said second fluorescence intensity spectrum with a peak fluorescence intensity value of said second fluorescence intensity spectrum.

8. The method of claim 7, wherein said second slope parameter is a function of an average slope in said predetermined portion of said normalized second fluorescence intensity spectrum.

9. The method of claim 1, said step of detecting tissue abnormality comprising, detecting tissue abnormality as a predetermined empirical discriminant function of said first and second slope parameters.

10. The method of claim 9, said step of detecting tissue abnormality comprising, detecting tissue abnormality as a predetermined linear empirical discriminant function of said first and second slope parameters.

11. An in vivo method of detecting tissue abnormality in a diagnostic cervical tissue sample in a patient, comprising:
    identifying a presumptively histologically normal cervical tissue sample from the patient;
    illuminating the diagnostic tissue sample and said presumptively histologically normal tissue sample with electromagnetic radiation;
    detecting a first fluorescence intensity spectrum from the diagnostic tissue sample;
    detecting a second fluorescence intensity spectrum from said presumptively histologically normal tissue sample;
    calculating a slope parameter indicative of tissue abnormality from said first fluorescence intensity spectrum;
    calculating an intensity parameter characteristic of normal tissue from said second fluorescence intensity spectrum;
    calculating a discriminant parameter as a function of said slope and intensity parameters;
    detecting tissue abnormality in the diagnostic cervical tissue sample by substituting said discriminant parameter in a predetermined discriminant function.

12. An in vivo method of detecting CIN in a diagnostic cervical tissue sample in a patient having presumptively known normal cervical tissue, comprising:
- illuminating the diagnostic tissue sample and presumptively known normal cervical tissue with electromagnetic radiation;
- detecting a first fluorescence intensity spectrum from the diagnostic tissue sample;
- detecting a second fluorescence intensity spectrum from the presumptively known normal cervical tissue;
- calculating from a predetermined portion of said first fluorescence intensity spectrum a first slope parameter which is indicative of CIN in the diagnostic cervical tissue sample;
- calculating from a predetermined portion of said second fluorescence intensity spectrum a second slope parameter which characterizes presumptively normal cervical tissue in the patient; and
- detecting CIN in the diagnostic cervical tissue sample as a function of said first and second slope parameters.

13. The method of claim 12, said illuminating step comprising, illuminating said diagnostic tissue sample with electromagnetic radiation having a wavelength of about 337 nm.

14. The method of claim 12, said step of calculating said first slope parameter comprising, calculating said first slope parameter from a portion of said fluorescence intensity spectrum corresponding to wavelengths between about 440 nm and about 460 nm.

15. The method of claim 12, said step of calculating said second slope parameter comprising, calculating said second slope parameter from a portion of said second fluorescence intensity spectrum corresponding to wavelengths between about 410 nm and about 430 nm.

16. The method of claim 12, wherein said first and second slope parameters are calculated after normalization of said first and second fluorescence intensity spectra to peak fluorescence intensity values of 1.

17. The method of claim 14, wherein said first and second slope parameters are functions of average slopes in said normalized first and second fluorescence intensity spectra respectively, said slopes being measured in predetermined regions of said normalized first and second fluorescence intensity spectra respectively, said regions lying substantially between wavelengths corresponding to said predetermined portions of said first and second fluorescence intensity spectra respectively.

18. The method of claim 12, said step of detecting CIN comprising, detecting CIN as a predetermined empirical discriminant function of said first and second slope parameters.

19. The method of claim 18, said step of detecting CIN comprising, detecting CIN as a predetermined linear empirical discriminant function of said first and second slope parameters.

20. An apparatus for in vivo detection of tissue abnormality in a diagnostic cervical tissue sample in a patient having presumptively known normal cervical tissue, comprising:
- means for applying electromagnetic radiation to a diagnostic cervical tissue sample and to presumptively known normal cervical tissue;
- radiation detection means for detecting a fluorescence intensity spectrum induced in the diagnostic cervical tissue sample, and for detecting a plurality of normal fluorescence intensity spectra induced in the presumptively known normal cervical tissue by said means for applying;
- a computer, connected to said means for applying and to said means for detecting, including,
  - means for measuring a peak normal fluorescence intensity value in each normal fluorescence intensity spectrum,
  - means for calculating an average peak normal fluorescence intensity from said peak normal fluorescence intensity values,
  - means for measuring a peak fluorescence intensity value from said fluorescence intensity spectrum induced in the diagnostic cervical tissue sample,
  - means for calculating from a predetermined portion of said fluorescence intensity spectrum a slope parameter, which is indicative of tissue abnormality,
  - means for calculating relative peak fluorescence intensity as a function of said peak fluorescence intensity value and said average peak normal fluorescence intensity, and
  - means for detecting tissue abnormality as a function of said slope parameter and said relative peak fluorescence intensity.

* * * * *

UNITED STATES PATENT AND TRADEMARK OFFICE
CERTIFICATE OF CORRECTION

PATENT NO. : 5,421,339

DATED : June 6, 1995

INVENTOR(S) : Nirmala Ramanujam *et al.*

It is certified that error appears in the above-identified patent and that said Letters Patent is hereby corrected as shown below:

On the title page, item [75] change "Michele F. Mitchell" to --Michele Follen Mitchell--

Signed and Sealed this

Nineteenth Day of September, 1995

Attest:

BRUCE LEHMAN

*Attesting Officer*          *Commissioner of Patents and Trademarks*